(12) United States Patent
Widlund et al.

(10) Patent No.: US 6,508,798 B1
(45) Date of Patent: *Jan. 21, 2003

(54) ABSORBENT ARTICLE

(75) Inventors: Urban Widlund, Mölnlycke (SE); Anders Gustafsson, Billdal (SE); Anna Svernlöv, Kullavik (SE)

(73) Assignee: Molnlycke AB, Gothenburg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/704,515
(22) PCT Filed: Mar. 17, 1995
(86) PCT No.: PCT/SE95/00273
§ 371 (c)(1), (2), (4) Date: Sep. 12, 1996
(87) PCT Pub. No.: WO95/25494
PCT Pub. Date: Sep. 28, 1995

(30) Foreign Application Priority Data

Mar. 18, 1994 (SE) .............................................. 9400917

(51) Int. Cl.⁷ ............................ A61F 13/15; A61F 13/20
(52) U.S. Cl. ......................... 604/385.27; 604/385.101; 604/385.19; 604/385.28
(58) Field of Search .......................... 604/317, 327–331, 604/346–358, 369, 374–375, 385.1, 385.2, 397, 399; 128/98.1; 602/67, 385.101, 385.19, 385.21–385.28

(56) References Cited

U.S. PATENT DOCUMENTS

| 2,829,647 A | 4/1958 | Dexter |
| 4,704,116 A | 11/1987 | Enloe |
| 4,895,568 A * | 1/1990 | Enloe ...................... 604/385.2 |

FOREIGN PATENT DOCUMENTS

| PT | 9202817 | * | 1/1994 | |
| WO | 9414395 | * | 7/1994 | .............. 604/385.1 |

OTHER PUBLICATIONS

Translation of Portugese 9202817-9.*

* cited by examiner

Primary Examiner—Glenn K. Dawson
Assistant Examiner—K. M. Reichle
(74) Attorney, Agent, or Firm—Young & Thompson

(57) ABSTRACT

An absorbent article having a front part (13; 13'), a rear part (14; 14') and a crotch part (15; 15') which lies therebetween. The article includes an absorbent body (1; 1'; 25) which is enclosed between an outer, liquid-impermeable casing sheet (7; 7'; 26) and an inner, liquid-permeable casing sheet (8; 8'; 27), this latter sheet lying proximal to a wearer's body in use. The article further includes on opposite sides of a longitudinal symmetry axis of the article flexible, longitudinally extending flaps (9, 10' 9', 10'; 28, 29), each of which is connected to the inner casing sheet along a longitudinal edge and which extends from the connected longitudinal edge in toward a longitudinal symmetry axis of the article. The flaps (9, 10; 9', 10'; 28, 29) are joined together in the crotch part (15; 15') of the article. The width of the flaps between the connected longitudinal edge and a free longitudinal edge of each flap is greatest in the crotch part (15; 15') and decreases progressively from the crotch part (15; 15') toward the respective front and rear parts (13, 14; 13', 14') whereby the flaps (9, 10; 9', 10'; 28, 29) taper toward the respective front and rear parts (13, 14; 13', 14') from a place at which the flaps are connected together such that adjacent free longitudinal edges of the flaps approach each other most closely at that place and diverge from each other longitudinally of the adjacent free longitudinal edges in directions away from that place when the absorbent article is flattened.

9 Claims, 3 Drawing Sheets

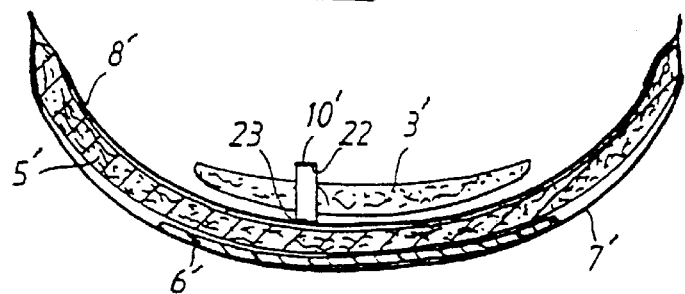
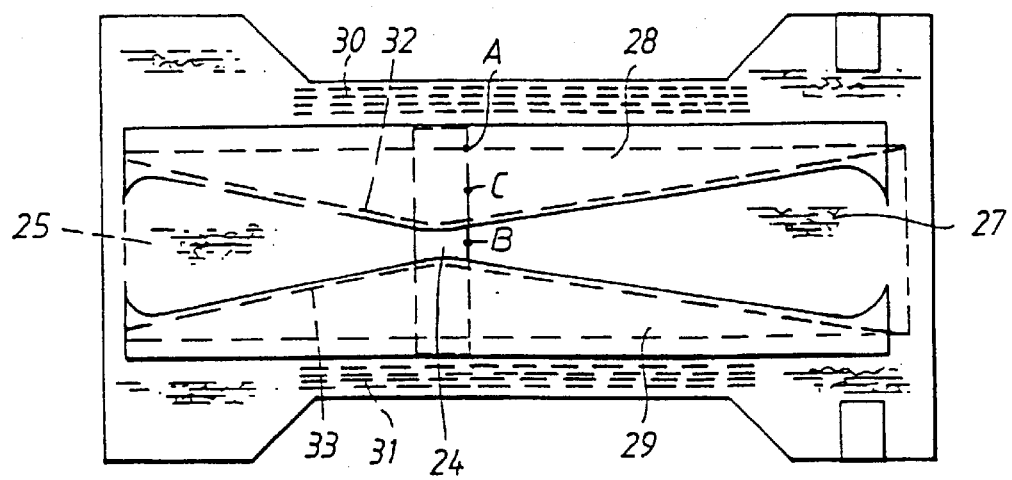
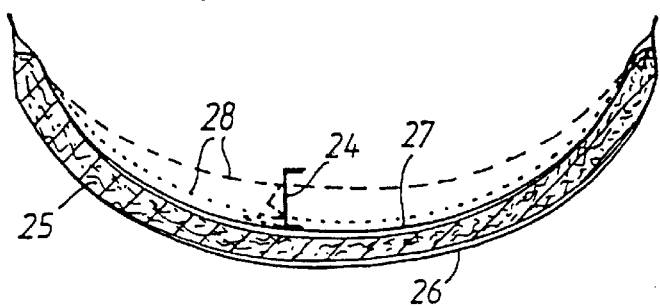

ABSORBENT ARTICLE

FIELD OF THE INVENTION

The present invention relates to an absorbent article, such as a diaper or an incontinence guard, which includes a front part, a rear part and a crotch part which lies therebetween, and which further includes an absorbent body which is enclosed between an outer, liquid-impermeable casing sheet and an inner, liquid-permeable casing sheet which latter sheet lies proximal to the wearer's body when the article is in use, and longitudinally extending flaps of flexible material located on both sides of the longitudinal symmetry axis of the article, wherein each of the flaps is attached to the inner casing sheet along one of its longitudinal edges, and wherein the flaps extend transversely in towards the longitudinal symmetry axis of the article from their respective attachment points.

BACKGROUND OF THE INVENTION

An absorbent article of this kind is known from U.S. Pat. No. 4,704,116. The flaps are intended to inhibit lateral flow of urine along the top sheet of the article and form side barriers which prevent lateral leakage of solid excrement. The flaps are also intended to form together with the inner casing sheet "containers" which isolate the skin of the wearer from contact with excrement stored therein.

The main object of the present invention is to improve the isolating properties of the flaps of an absorbent article of this kind.

SUMMARY OF THE INVENTION

This object is achieved with an absorbent article of the kind defined in the introduction which is characterized in that the flaps are joined to one another in the crotch part of the article. This construction reduces the risk of the flaps being brought to a wrong position when putting on the article or as a result of undesirable lateral movement whilst the article is worn. Furthermore, the join between the flaps is operative in retaining the mutual distances between the mutually facing edges of the flaps whilst the article is worn.

According to one preferred embodiment of the invention, the flaps are joined by means of a narrow strip of liquid-permeable or liquid-impermeable material and are tapered from their respective points of attachment towards respective front and rear article parts. The join or connection between the flaps is located longitudinally between the wetting point and the fecal discharge point, and the flaps extend longitudinally from a forward part of the front article part to a rearward part of the rear article part. Elastic devices in the form of elastic threads extend preferably along the mutually facing longitudinal edges of the flaps.

According to another advantageous embodiment, the join between the flaps is effected with a piece of material which is attached to the flaps and to the inner casing sheet respectively along its opposing edges by means of transverse attachment lines. In this embodiment, when the article is worn the piece of material will form a wall which delimits the rear article part from its front part and therewith prevents contact between urine and feces.

BRIEF DESCRIPTION OF THE DRAWINGS

The invention will how be described in more detail with reference to the accompanying drawings, in which

FIGS. 4 and 5 are views corresponding to the views presented in FIGS. 2 and 3 and illustrate a second embodiment of an inventive diaper; and FIGS. 6 and 7 are views corresponding to the views presented in FIGS. 2 and 3 and illustrate a third embodiment of an inventive diaper.

DETAILED DESCRIPTION OF THE PREFERRED EMBODIMENTS

Figure 1:
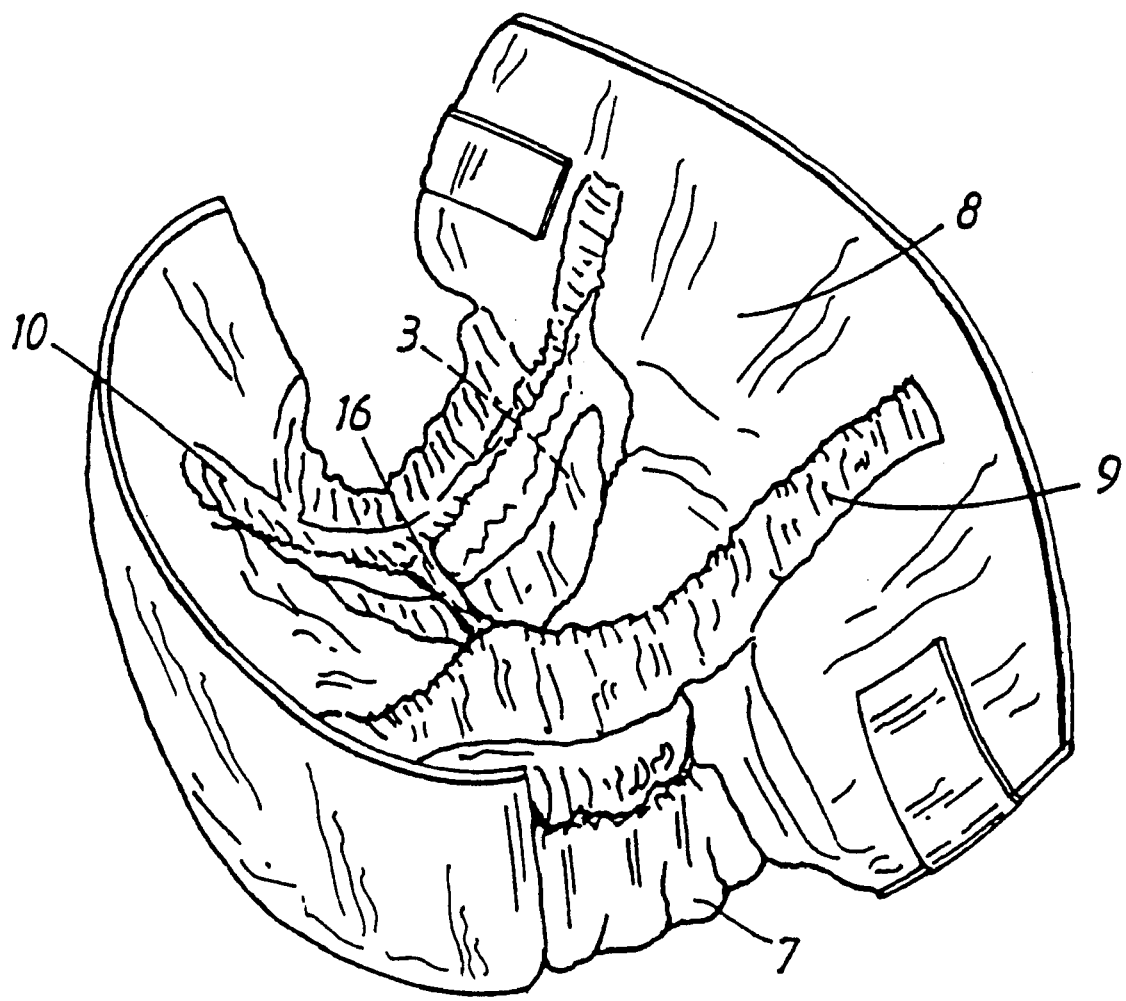
FIG. 1 is a schematic perspective view of one embodiment of an inventive diaper, taken obliquely from above.
Figure 2:
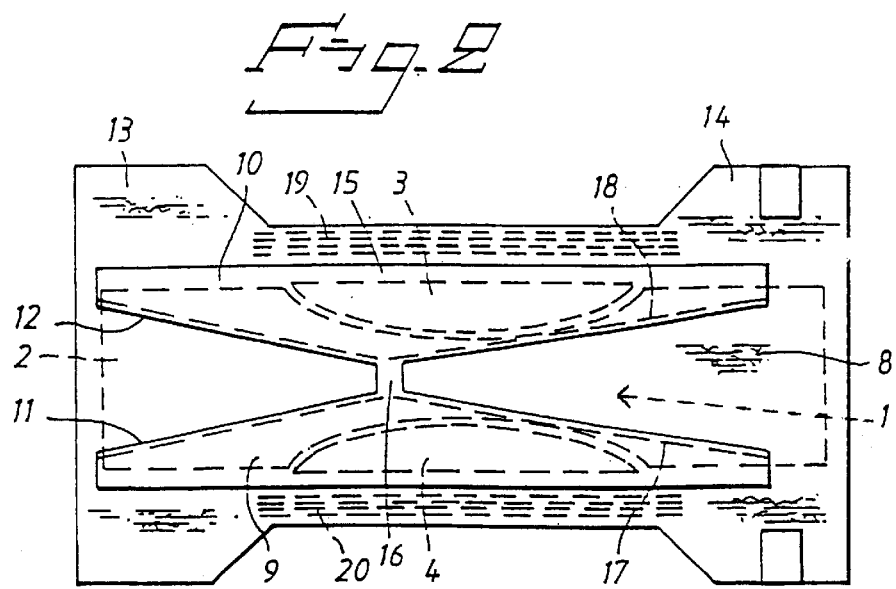
FIG. 2 is a schematic illustration of the diaper shown in FIG. 1 taken from above with the diaper in a flat state.
Figure 3:
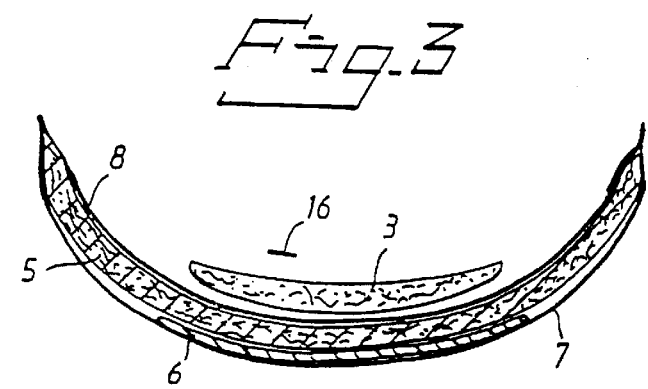
FIG. 3 is a schematic longitudinal sectional view of the diaper shown in FIG. 1.

The diaper illustrated in FIGS. 1–3 includes an absorbent body 1 which in the case of the illustrated embodiment is comprised of an hourglass-shaped main body 2 and two side bodies 3, 4. The main body 2 is comprised of two sheets 5, 6. The upper sheet 5 and the side bodies 3, 4 are comprised of air-laid cellulose fluff. The bottom sheet 6 is preferably comprised of air-laid cellulose fibres and is preferably compressed more heavily than the upper sheet 5. Alternatively, the bottom sheet 6 may be comprised of absorbent reel material of the type described in Swedish Patent Application No. 9203445-3, this material including a dry-formed sheet containing 5–100% cellulose fibres which has a density of between 0.2–1.0 g/cm$^3$ and a surface weight between 30–2000 g/m$^2$ and which has been formed by compressing a cellulose-fibre containing web without subsequent defibration and fluff building. The reader is referred to the aforesaid patent application for a closer study of this type of reel material. As will be seen from FIG. 4, the sheet 6 is rectangular in shape and extends beneath only a part of the sheet 5.

The absorbent body 1 is enclosed between an outer casing sheet or bottom sheet 7 of liquid-impermeable material, for instance polyethylene plastic, and an inner liquid-permeable casing sheet 8, which is preferably made of nonwoven material. The sheet 8 is preferably similar to the bottom sheet 7 and the sheets are joined together at parts which lie outside the absorbent body 1. As will best be seen from FIG. 2, the side bodies 3, 4 are located laterally slightly beyond the main body 2 and the casing sheets 7, 8 are joined together in the gap presented between the main body and the side bodies.

The diaper also includes two longitudinally extending flaps 9, 10 which are attached to the inner casing sheet 8 at their mutually distal longitudinal edges and at their ends. The mutually proximal longitudinal edges 11, 12 of the flaps 9, 10 extend convergently towards one another from respective ends of the diaper front part 13 and the diaper rear part 14, to a point in the crotch region 15 at which the flaps are joined together by a strip of material 16. The flaps and the strip are preferably made of the same material as the inner casing sheet, although this is not a necessary feature, since the flaps and the strip can be made from any suitable flexible and skin-friendly sheet material. An elastic thread 17, 18 extends along the respective edges 11, 12 of each flap 9, 10. It will be understood that more elastic threads and/or other types of elastication, such as elastic ribbon, ribbons of film having elastic properties, etc., may be used in place of the single threads 17, 18.

The strip 16 is located between the diaper wetting point and fecal discharge point. By wetting point is meant that region of the diaper within which urine can be expected to be discharged when the diaper is positioned correctly on the wearer, while correspondingly by fecal discharge point is meant that region within which feces will be discharged when the diaper is correctly positioned, i.e. the regions that lie opposite the urethra orifice and the anus of the wearer while taking into account normal variations of the wearer's anatomy within the size range of the user for which the diaper is dimensioned.

The two elastic threads 17, 18 of flaps 9, 10 are attached to the flaps in a stretched or tensioned state with the aid of narrow strips of nonwoven material (not shown) which are glued to the threads and respective flaps or attached in some other suitable way. In the illustrated embodiment, the strips are disposed along the full length of the threads and the threads are thus attached to the flaps along the whole of their length. This is not absolutely necessary, however, since the desired function can also be achieved by fastening the threads to the flaps at their respective ends and within the region of the strip 16.

According to one variant, the nonwoven strips form guide passages for elastic threads extending therethrough. In this case, it is sufficient to fasten the threads to the top sheet at the ends of the passages. Thus, when the strips extend along the full length of the threads, it is sufficient to fasten the ends of the threads to the ends of the flaps. The threads will preferably extend freely in the aforesaid guide passages, which can be formed by folding edge parts of the flaps so as to form the nonwoven strips integrally with the flaps.

The elastic threads can also be fastened directly to the top sheet by the technique known from Swedish patent Application No. 9304232-3 filed on Dec. 21, 1993. This Application describes how elastic elements can be joined directly to an underlying substrate with the aid of thermoplastic components which are secured to the elastic elements by mechanical locking or by chemical adhesion and which are joined to an underlying substrate, preferably by ultrasonic welding. The reader is referred to this last-mentioned Swedish patent application for a closer study in this regard.

As will be seen from FIGS. 1 and 2, the diaper includes leg elastication in the form of elastic devices 19, 20 which extend along the side edges of the crotch part 15 and along a part of respective front and rear diaper parts 13 and 14. In the illustrated case, the elastic devices are comprised of four elastic threads which have been attached in a stretched state between the outer casing sheet 7 and the inner casing sheet 8 and fastened to these sheets. It will be understood that the leg elastication may comprise more or fewer than four elastic threads, and that other types of elastic devices, such as elastic ribbon, film ribbon having elastic properties, etc., may also be used.

FIG. 2 shows the diaper in a flat state, by which is meant the state which the diaper has during manufacture, in which the diaper is held stretched against the spring restoring forces exerted by the elastic devices mounted thereon. When the finished diaper is released from these holding forces, the elastic devices 17–20 strive to contract to a fully relaxed state and will thereby bring the diaper to the shape shown in FIGS. 1 and 3.

Contraction of the threads 17, 18 results in shortening and gathering of the flaps 9, 10. Shortening of the flaps is enabled by curving of the main body 2 of the absorbent body 1 at the same time as the side bodies 3, 4 swing upwards about respective hinges formed by the casing sheets 7, 8 joined in the gap presented between respective bodies 3, 4 and the main body 2. Because the flaps are joined together by strip 16, the mutually facing longitudinal flap edges 11, 12 will extend convergently towards each other, away from respective front and rear diaper parts and towards the region of the strip 16, even after the flaps have been gathered or likewise folded by contraction of the elastic threads 17, 18. Furthermore, the connection achieved between the flaps by means of the strip 16 means that the flaps will not be raised or lifted from the inner casing sheet 8 to the same extent as when the flaps are not joined together.

It is pointed out in this regard that FIG. 1 shows the diaper in the absence of any load thereon and not in the state that it adopts when worn. The shape adopted by the diaper when worn will naturally depend on the anatomy of the wearer and the diaper is dimensioned so that, in a normal case, the elastic threads 17, 18 will be stretched slightly when putting on the diaper. However, the length of the diaper is such that a large part of the folds in the flaps will remain after putting on the diaper, so that the flaps will be spaced from the inner casing sheet 8 along a greater part of its extent, even after putting on the diaper.

Thus, when the diaper is worn, there is located between the flaps and the inner casing sheet a space in which urine and feces can be held without coming into contact with the wearer's skin. It will be understood that the distance between the mutually opposing flap edges 11, 12 behind the strip 16, particularly at the fecal discharge point, is of decisive significance in ensuring that discharged excrement will land in this space and not on the upper surfaces of the flaps. It has been found that the distance between these edges should lie at least 3 cm at the fecal discharge point, while the rear edge of the strip 16 should lie at least 1 cm and preferably 2 cm in front of the fecal discharge point, and that the strip should have a length of at least 2 cm. Because the elastic threads 17, 18 exert a spring force in both the longitudinal and the transverse direction of the diaper, both the strip and the long edges 11, 12 of the flaps are held stretched when the diaper is worn, so as to ensure that the aforesaid distances are maintained when the diaper is in use. In order to achieve a high stretching effect, the ends of the flaps, and therewith also the ends of the threads 17, 18, will preferably lie transversely on a level with the longitudinally extending edges of the absorbent body 1.

In addition to gathering the flaps 9, 10, the elastic threads 17, 18 also provide a sealing function, by lying against the wearer's body when the diaper is worn. This greatly reduces the risk of urine discharged by male wearers landing on the upper sides of the flaps and running along said surfaces instead of being deposited on the inner casing sheet and there be absorbed by the absorbent body. Because the threads extend along the longitudinal edges of the flaps 11, 12, the risk of the position of the flaps changing from the position taken when putting on the diaper, as a result of external loads to which the diaper is subjected as a result of wearer movement for instance, is also reduced at the same time. Another advantage is that if the absorbent body is pressed against the wearer's body by an external load, it is more difficult for urine and feces to leak over the flap edges. 11, 12 and onto the upper surfaces of the flaps and there mix together. It has been found that in order to achieve these sealing functions, the distance between the longitudinal edges 11, 12 of the flaps at the centre of the fecal discharge point should be 6 cm, at the most, and is preferably less than 5 cm. The length of the narrow strip 16 will preferably not exceed 4 cm. The strip 16 may also be comprised of elastic material, so as to ensure that the strip 16 will seal against the body. However, this is not necessary in the case of the illustrated configuration, since the elastic threads 17, 18 hold the strip tensioned and pressed against the wearer's body, as before mentioned.

From an absorption aspect, the side bodies 3, 4 are not joined to the remainder of the absorbent body 1 and form safety bodies which absorb liquid when the main absorbent body becomes saturated or is unable to absorb the fluid discharged for some other reason. In addition to this function, the side bodies contribute towards the stability of the basin formed by contraction or gathering of the flaps, and prevents the whole of the main body from lying against the wearer's body when the diaper is subjected to external load.

In the case of the embodiment illustrated in FIGS. 1–3, the flaps 9, 10 and the strip are formed integrally with one another. As will be understood, this is not absolutely necessary since the strip 16 may be fastened to the flaps in any suitable manner, for instance by gluing, and may even be made of a different material.

Figure 4:
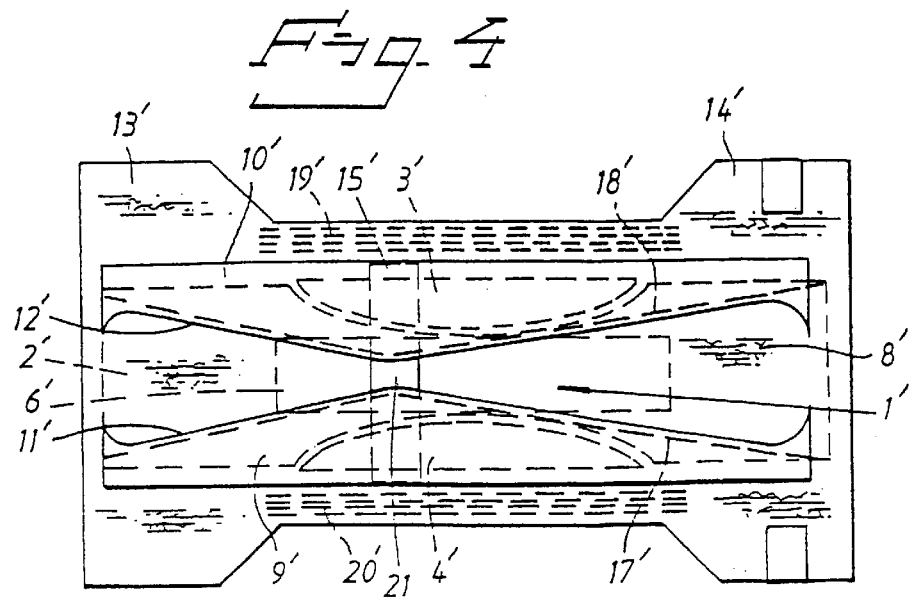

FIGS. 4 and 5 illustrate a second embodiment of the invention which differs from the embodiment illustrated in FIGS. 1–3 mainly by virtue of the fact that the flaps have been joined together in a slightly different way. In FIGS. 4 and 5, those elements which correspond functionally to similar elements in the embodiment illustrated in FIGS. 1–3 have been identified by the same reference signs to which a prime has been added.

In the embodiment illustrated in FIGS. 4 and 5, a tubular body 21 is mounted in a flattened state between the underside of the flaps 9', 10' and the inner casing sheet 8', and extends transversely between the attachments of the flaps to the casing sheet 8' and is located longitudinally between the wetting point and the fecal discharge point. The upper and underside of the tubular body 21 are respectively fastened to the underside of the flaps and to the inner casing sheet 8' by means of a connection or join which has a small extent in the longitudinal direction of the diaper, e.g. by means of a glue bead or strand.

Since the upper side and the underside of the tubular body 21 are fastened respectively to the flaps and to the inner casing sheet 8 along a narrow bead 22 and 23 respectively, these parts of the tubular body will also be distanced from one another in a manner corresponding to these elements when the elastic threads 17', 18' contract. This causes the tubular body to be raised or unfolded from its flattened state shown in FIG. 4. The tubular body of the illustrated embodiment is so dimensioned that in the diaper configuration illustrated in FIG. 5, said body is so raised as to be practically completely flattened in the longitudinal symmetry plane of the diaper in a plane at right angles to this symmetry plane and to the absorbent body 1', as will be seen from said Figure. The tubular body 21 is lifted successively from its flattened state shown in FIG. 4 in a direction towards the mutually opposed longitudinal edges 11', 12' of the flaps and is highest between these edges, as will be seen from FIG. 5 which shows the tubular body fully raised at the part thereof that is located between the flaps. In this embodiment, the tubular body will thus be folded or gathered to a desired extent in a direction towards the diaper edges. According to one variant, the tubular body can be given a circumference which decreases successively in a direction towards the side edges of the diaper, from a central part delimited by the longitudinal edges 11', 12' of the flaps 9', 10'.

The tubular body 21 forms a barrier which delimits the spaces beneath the flaps 9', 10' from one another in the longitudinal direction. This prevents urine and feces from mixing together. If urine and feces mix, enzymes in the feces will split or cleave the urea in the urine, therewith forming ammonia. This would result in a higher pH, which in turn would result in greater activity of the enzymes protease and lipase in the excrement, which would give rise to greater skin irritation should excrement come in contact with the skin. The arrangement also ensures that excrement will not be deposited in the space in front of the tubular body 21 and thereby come into contact with the genitals of the wearer.

The tubular body 21 may be comprised of liquid-impermeable or liquid-permeable material and is conveniently comprised of the same material as that used for the outer casing sheet, the inner casing sheet or the flaps. Instead of using a tubular body 21, which provides a two-wall barrier as illustrated in FIG. 5, the barrier may be comprised of a single wall of flexible material which is mounted in a folded or corrugated state, for instance a bellows-like state, between the inner casing sheet and the flaps and fastened thereto in the same manner as the tubular body 21.

FIGS. 6 and 7 are views corresponding to the views shown in FIGS. 2 and 3 and illustrate a diaper which is provided with one such single-wall or sheet-like barrier 24. The diaper illustrated in these Figures includes a rectangular absorbent body 25 which is enclosed between outer and inner casing sheets 26 and 27, and further includes two flaps 28, 29 which correspond to the flaps 9', 10' of the embodiment illustrated in FIGS. 4 and 5 and which are attached to the inner casing sheet 27. The diaper includes leg elastic 30, 31 and elastic elements 32, 33, similar to the earlier described diapers. The barrier 24 is comprised of a rectangular piece of liquid-impermeable or liquid-permeable material, which in the form of a single fold is mounted between the flaps and the inner casing sheet in the same manner as that described for the tubular body 21. Lifting of the material piece 24 as a result of gathering of the flaps at a point A in the proximity of the side edge of the absorbent body and respectively at a point B located between the side edges of the absorbent body is indicated in dotted and full lines respectively, while lifting of the material piece at a point C between these positions is indicated in broken lines in FIG. 7. In the embodiment illustrated in FIGS. 4 and 6, the mutually opposing longitudinal edges of the flaps 9' 10' and 28, 29 respectively extend arcuately at their end parts. This configuration is, of course, also possible for the embodiment illustrated in FIGS. 1–3.

It will be understood that the aforedescribed and illustrated embodiments of the invention can be modified within the scope of the invention. For instance, the flaps may be formed integrally with the inner casing sheet, and the absorbent body can be given a different construction and configuration than that shown. The tubular body may also be formed by a fold in the inner casing sheet, which has been sealed at that part adjoining the remainder of the sheet concerned and fastened to the flaps in conjunction with mounting the same. The shapes and the dimensions of the flaps can also be varied. It will also be understood that the invention can be applied with diapers whose absorbent bodies have a different construction and shape from that shown, for instance rectangular absorbent bodies comprising one or more absorbent layers with or without an admixture of so-called superabsorbent materials. The invention can also be applied with so-called pants-like diapers or training pants, and with incontinence guards. The invention is therefore restricted solely by the content of the following Claims.

What is claimed is:

1. In an absorbent article having a front part (13; 13'), a rear part (14; 14') and a crotch part (15; 15') which lies therebetween, the article further including an absorbent body (1; 1'; 25) which is enclosed between an outer, liquid-impermeable casing sheet (7; 7'; 26) and an inner, liquid-permeable casing sheet (8; 8'; 27), this latter sheet lying proximal to a wearer's body in use, and the article further including on opposite sides of a longitudinal symmetry axis of the article flexible, longitudinally extending flaps (9, 10; 9', 10'; 28, 29), each of which is connected to the inner casing sheet along a longitudinal edge and extends from said connected longitudinal edge in toward the longitudinal symmetry axis of the article, the flaps (9, 10; 9', 10'; 28, 29) being connected together in the crotch part (15; 15') of the article; the improvement wherein the width of the flaps between said connected longitudinal edge and a free longitudinal edge of each flap is greatest in said crotch part (15; 15') and decreases progressively from said crotch part in opposing directions (15; 15') toward said front and rear parts (13, 14; 13', 14') wherein the flaps (9, 10; 9', 10'; 28, 29) taper toward said front and rear parts (13, 14; 13', 14') from the place at which said flaps are connected together such that said free longitudinal edges approach each other most closely at said place and diverge from each other longitudinally of said free longitudinal edges in opposing directions away from said place when the absorbent article is flattened.

2. An article according to claim 1, wherein the connection between the flaps (9, 10) is comprised of a narrow strip (16) of liquid-permeable or liquid-impermeable material.

3. An article according to claim 1, wherein the connection (16; 21; 24) between the flaps (9, 10; 9', 10'; 28, 29) is located longitudinally between a wearer's wetting point in use and a wearer's fecal discharge point in use.

4. An article according to claim 1, wherein the flaps (9, 10; 9', 10', 28, 29) extend longitudinally from a forward part of said front article part (13; 13') to a rear part of said rear article part (14; 14').

5. An article according to claim 1, wherein the connection (21; 24) between the flaps (9', 10'; 28, 29) is comprised of a piece of material which is attached along opposing edges to the flaps and to the inner casing sheet respectively by means of transverse connection lines (22, 23).

6. An article according to claim 5, wherein said material piece (21; 24) connecting the flaps (9', 10'; 28, 29) extends transversely from one to the other of said longitudinal edges of the flaps connected to the inner casing sheet (8'; 27), such that the material piece (21; 24) will form a barrier between a front and a rear space defined by the flaps and the underlying absorbent body (1'; 25).

7. An article according to claim 1, wherein elastic devices (17, 18; 17', 18'; 32, 33) extend along said free longitudinal edges (11, 12; 11', 12') of the flaps (9, 10; 9', 10'; 28, 29).

8. An article according to claim 7, wherein said elastic devices (17, 18; 17', 18'; 32, 33) are comprised of elastic threads.

9. An article according to claim 1, wherein the connection (16) between the flaps (9, 10) is elastic.

* * * * *